(12) United States Patent
Conrado et al.

(10) Patent No.: US 10,808,263 B2
(45) Date of Patent: Oct. 20, 2020

(54) PROCESSES AND SYSTEMS FOR METABOLITE PRODUCTION USING HYDROGEN RICH C1-CONTAINING SUBSTRATES

(71) Applicant: LanzaTech, Inc., Skokie, IL (US)

(72) Inventors: Robert John Conrado, Skokie, IL (US); Guy William Waters, Skokie, IL (US); Matthew Puglisi, Skokie, IL (US); Joshua Jeremy Conolly, Skokie, IL (US)

(73) Assignee: LANZATECH, INC., Skokie, LA (US)

( * ) Notice: Subject to any disclaimer, the term of this patent is extended or adjusted under 35 U.S.C. 154(b) by 0 days.

(21) Appl. No.: 16/123,464

(22) Filed: Sep. 6, 2018

(65) Prior Publication Data

US 2019/0078121 A1 Mar. 14, 2019

Related U.S. Application Data

(60) Provisional application No. 62/556,099, filed on Sep. 8, 2017.

(51) Int. Cl.
| | | |
|---|---|---|
| *C12P 7/14* | (2006.01) | |
| *C12R 1/145* | (2006.01) | |
| *C12P 7/06* | (2006.01) | |
| *C12P 7/16* | (2006.01) | |
| *A23K 10/12* | (2016.01) | |
| *C12P 7/08* | (2006.01) | |

(Continued)

(52) U.S. Cl.
CPC ............... *C12P 7/14* (2013.01); *A23K 10/12* (2016.05); *A23K 10/16* (2016.05); *C12N 1/20* (2013.01); *C12N 1/30* (2013.01); *C12P 7/00* (2013.01); *C12P 7/065* (2013.01); *C12P 7/08* (2013.01); *C12P 7/16* (2013.01); *C12P 7/54* (2013.01); *C12R 1/02* (2013.01); *C12R 1/145* (2013.01)

(58) Field of Classification Search
CPC . C12N 1/20; C12N 15/52; C12N 9/88; C12N 1/02; C12N 1/30; C12N 1/38; C12N 9/0016; C12N 9/1018; C12N 9/1029; C12N 9/1217; C12N 9/78; C12N 9/90; C12N 9/16; C12N 15/00; C12N 15/74; C12N 2510/02; C12N 9/0006; C12N 9/0083; C12N 9/1022; C12N 9/0067; C12N 9/0004; C12N 9/1025; C12P 7/54; C12P 1/04; C12P 7/16; C12P 13/005; C12P 7/04; C12P 7/42; C12P 7/62; C12P 5/026; C12P 7/00; C12P 7/08; C12P 7/14; C12P 7/26; C12P 7/40; C12P 7/56; C12P 7/065; C12P 7/649; C12P 13/06; C12P 13/08; C12P 5/002; C12P 7/46; C12P 7/48; C12P 7/50; C12P 7/6409; C12P 3/00; C12P 5/00; C12P 5/023; C12P 7/18; C25B 15/08; C25B 1/00; C25B 1/003; C25B 1/04; C25B 1/02; Y02E 50/17; Y02E 60/366; Y02E 50/13; Y02E 50/343; Y02E 50/10; C12M 21/12; C12M 43/00; C12M 45/07; C12M 29/26; C12M 41/34; C12M 43/04; C12M 47/02; C12M 47/10; C12M 47/18; C12M 29/18; C12M 29/24; C12M 23/40; C12M 25/00; C12M 29/02; C12M 29/20; C12M 41/44; C12M 41/46; C12M 41/48; C12M 29/04; C12M 23/58; C12Y 401/0304; C12Y 402/99021; C12Y 504/04002; C12Y 504/99005; C12Y 104/01012; C12Y 201/03003; C12Y 207/02002; C12Y 305/03006; C12Y 501/01012; C12Y 504/03005; C12Y 101/01004; C12Y 114/99033; C12Y 202/01006; C12Y 301/02014; C12Y 401/01005; C12Y 112/07002; C12Y 101/01001; C12Y 101/01002; C12Y 102/07005; C12Y 203/01008; C12Y 207/02001; Y02P 20/133; Y02P 20/52; A23K 10/12; A23K 10/16; B01D 19/0057; B01D 3/002; B01D 3/10; B01D 53/14; C01B 2203/043; C01B 2203/0475; C01B 2203/0485; C01B 2210/0051; C01B 2210/0064; C01B 2210/0067; C01B 2210/007; C01B 3/38; C12R 1/02; C12R 1/145

See application file for complete search history.

(56) References Cited

U.S. PATENT DOCUMENTS 9,617,566 B2 * 4/2017 Collet .................... G16B 99/00
9,834,792 B2 * 12/2017 Trevethick ............. C12M 29/18
(Continued)

*Primary Examiner* — Deborah K Ware
(74) *Attorney, Agent, or Firm* — Frank S. Molinaro

(57) ABSTRACT

The invention is directed to a process for producing one or more fermentation product in a multi-stage process including an inoculation reactor and at least one bioreactor. The inoculation reactor is fed a C1-containing gaseous substrate containing a reduced amount of hydrogen. The hydrogen is reduced to increase the proportion of CO in the C1-containing gaseous substrate being provided to the inoculation reactor. The inoculation reactor ferments the CO-rich C1-containing gaseous substrate and produces an inoculum, which is fed to at least one bioreactor. The bioreactor receives the C1-containing gaseous substrate, which may or may not contain reduced amounts of hydrogen, to produce one or more fermentation product. By providing a CO-rich C1-containing gaseous substrate to the inoculation reactor, both the inoculation reactor and the subsequent bioreactor(s), are able to have increased stability and product selectivity.

10 Claims, 9 Drawing Sheets

(51) Int. Cl.
*C12R 1/02* (2006.01)
*C12N 1/20* (2006.01)
*C12N 1/30* (2006.01)
*C12P 7/54* (2006.01)
*A23K 10/16* (2016.01)
*C12P 7/00* (2006.01)

(56) References Cited

U.S. PATENT DOCUMENTS

| | | | |
|---|---|---|---|
| 10,174,303 B2* | 1/2019 | Behrendorff | C12P 1/04 |
| 10,358,662 B2* | 7/2019 | Simpson | C12P 7/54 |
| 2012/0252082 A1* | 10/2012 | Simpson | C12P 7/18 |
| | | | 435/140 |
| 2016/0010116 A1* | 1/2016 | Collet | G16B 99/00 |
| | | | 435/161 |
| 2016/0115505 A1* | 4/2016 | Trevethick | C12M 29/18 |
| | | | 435/140 |
| 2016/0338380 A1* | 11/2016 | Simpson | A23K 50/30 |
| 2016/0348087 A1* | 12/2016 | Behrendorff | C12P 1/04 |
| 2017/0159083 A1* | 6/2017 | Valgepea | C12P 7/40 |
| 2017/0175064 A1* | 6/2017 | Collet | C12M 41/26 |
| 2017/0218404 A1* | 8/2017 | Simpson | C12P 7/54 |

\* cited by examiner

PROCESSES AND SYSTEMS FOR METABOLITE PRODUCTION USING HYDROGEN RICH C1-CONTAINING SUBSTRATES

CROSS-REFERENCE TO A RELATED APPLICATION

The application claims the benefit of U.S. Provisional Application No. 62/556,099 filed Sep. 8, 2017, the contents of which are hereby incorporated by reference.

FIELD OF THE INVENTION

The invention relates to a process for producing one or more fermentation product through a multi-stage gas fermentation process including an inoculation reactor and at least one bioreactor. In particular, the invention relates to a process whereby a CO-rich C1-containing gaseous substrate is fed to the inoculation reactor to produce an inoculum.

BACKGROUND OF THE INVENTION

Carbon dioxide ($CO_2$) accounts for about 76% of global greenhouse gas emissions from human activities, with methane (16%), nitrous oxide (6%), and fluorinated gases (2%) accounting for the balance (the United States Environmental Protection Agency). Reduction of greenhouse gas emissions, particularly $CO_2$, is critical to halting the progression of global warming and the accompanying shifts in climate and weather.

It has long been recognized that catalytic processes, such as the Fischer-Tropsch process, may be used to convert gases containing carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of such gases. In particular, C1-fixing microorganisms have been demonstrated to convert gases containing $CO_2$, CO, and/or $H_2$ into products such as ethanol and 2,3-butanediol.

Such gasses may be derived, for example, from industrial processes, including gas from carbohydrate fermentation, gas from cement making, pulp and paper making, steel making, oil refining and associated processes, petrochemical production, coke production, anaerobic or aerobic digestion, synthesis gas (derived from sources including but not limited to biomass, liquid waste streams, solid waste streams, municipal streams, fossil resources including natural gas, coal and oil), natural gas extraction, oil extraction, metallurgical processes, for production and/or refinement of aluminium, copper, and/or ferroalloys, geological reservoirs, and catalytic processes (derived from steam sources including but not limited to steam methane reforming, steam naphtha reforming, petroleum coke gasification, catalyst regeneration-fluid catalyst cracking, catalyst regeneration-naphtha reforming, and dry methane reforming).

With particular industrial processes, the composition of the gas may not be ideal for fermentation. When the composition of the gas is not ideal, cell growth, product selectivity, and stability may be less than optimal.

Accordingly, there remains a need for an invention which optimizes the composition of gas from industrial processes to promote cell growth, product selectivity, and stability in a downstream fermentation process.

BRIEF SUMMARY OF THE INVENTION

The invention provides a process for producing one or more fermentation product, wherein a CO-rich C1-containing gaseous substrate is passed to an inoculation reactor comprising a liquid nutrient medium containing a culture of one or more C1-fixing microorganism where the CO-rich C1-containing gaseous substrate is fermented to produce an inoculum, at least a portion of the inoculum is passed to a bioreactor system, the bioreactor system defining at least one bioreactor containing a culture of one or more C1-fixing microorganism in a liquid nutrient medium, an $H_2$ rich C1-containing gaseous substrate is passed to the bioreactor system where the $H_2$ rich C1-containing gaseous substrate is fermented to produce at least one fermentation product.

In particular embodiments, the CO-rich C1-containing gaseous substrate being passed to the inoculation reactor comprises $H_2$ at an $H_2$:CO molar ratio of less than 1:1.

In certain instances, the CO-rich C1-containing gaseous substrate being passed to the inoculation reactor comprises $H_2$ at an $H_2$:CO molar ratio of less than 0.5:1.

Preferably, the CO rich C1-containing gaseous substrate being passed to the inoculation reactor comprises $H_2$ at a $H_2$:CO molar ratio between 0.02:1 to 1:1. In certain embodiments, the $H_2$:CO molar ratio is between 0.05:1 to 1:1, or 0.15:1 to 1:1, or 0.25:1 to 1:1, or 0.35:1 to 1:1, or 0.45:1 to 1:1, or 0.55:1 to 1:1, or 0.65:1 to 1:1, or 0.75:1 to 1:1, or 0.85:1 to 1:1, or 0.95:1 to 1:1.

In particular embodiments, the $H_2$ rich C1-containing gaseous substrate being passed to the bioreactor system comprises $H_2$ at an $H_2$:CO molar ratio of at least 1.1:1.

Preferably, the $H_2$ rich C1-containing gaseous substrate being passed to the bioreactor system comprises $H_2$ at an $H_2$:CO molar ratio between 1.1:1 to 6:1. In certain embodiments, the $H_2$:CO molar ratio is between 1.5:1 to 6:1, or 2:1 to 6:1, or 2.5:1 to 6:1, or 3:1 to 6:1, or 3.5:1 to 6:1, or 4:1 to 6:1, or 4.5:1 to 6:1, or 5:1 to 6:1.

In at least one embodiment, the C1-fixing microorganism in the either, or both, the inoculation reactor or the bioreactor system is a carboxydotrophic bacterium.

In embodiments where the C1-fixing microorganism is carboxydotrophic, the carboxydotrophic bacterium may be selected from the group consisting of *Moorella, Clostridium, Ruminococcus, Acetobacterium, Eubacterium, Butyribacterium, Oxobacter, Methanosarcina*, and *Desulfotomaculum*.

Preferably, the carboxydotrophic bacterium is *Clostridium autoethanogenum*.

In at least one embodiment, the bioreactor system comprises one or more primary bioreactors linked to one or more secondary bioreactors.

Preferably, the process provides for the passing of at least a portion of a C1-containing gaseous substrate to an inoculation reactor and at least a portion of the C1-containing gaseous substrate to a bioreactor, where the C1-containing gaseous substrate in the inoculation reactor is fermented to produce an inoculum, where at least a portion of the inoculum is passed to at least one bioreactor where the C1-containing gaseous substrate in the bioreactor is fermented to produce at least one fermentation product, and wherein the C1-containing gaseous substrate being passed to the inoculation reactor is subjected to at least one $H_2$ removal process prior to being passed to the inoculation reactor.

In particular embodiments, the C1-containing gaseous substrate being passed to the inoculation reactor comprises $H_2$ at an $H_2$:CO molar ratio of less than 1:1.

In certain instances, the C1-containing gaseous substrate being passed to the inoculation reactor comprises $H_2$ at an $H_2$:CO molar ratio of less than 0.8:1.

In certain instances, the C1-containing gaseous substrate being passed to the inoculation reactor comprises $H_2$ at an $H_2$:CO molar ratio of less than 0.5:1.

Preferably, the C1-containing gaseous substrate being passed to the inoculation reactor comprises $H_2$ at a $H_2$:CO molar ratio between 0.02:1 to 1:1. In certain embodiments, the $H_2$:CO molar ratio is between 0.05:1 to 1:1, or 0.15:1 to 1:1, or 0.25:1 to 1:1, or 0.35:1 to 1:1, or 0.45:1 to 1:1, or 0.55:1 to 1:1, or 0.65:1 to 1:1, or 0.75:1 to 1:1, or 0.85:1 to 1:1, or 0.95:1 to 1:1.

In certain embodiments, the $H_2$ removal process comprises at least one pressure swing adsorption process.

In certain embodiments, the $H_2$ removal process comprises at least one membrane separation module.

Preferably, at least a portion of the C1-containing gaseous substrate is derived from an industrial source.

In certain instances, at least a portion of the C1-containing gaseous substrate may be derived from at least one industrial source selected from the group consisting of carbohydrate fermentation, gas fermentation, cement making, pulp and paper making, steel making, oil refining and associated processes, petrochemical production, coke production, anaerobic or aerobic digestion, synthesis gas, natural gas extraction, oil extraction, metallurgical processes, for production and/or refinement of aluminium, copper, and/or ferroalloys, geological reservoirs, and catalytic processes.

Preferably, the process produces at least one fermentation product selected from the group consisting of: ethanol, acetate, butanol, butyrate, 2,3-butanediol, 1,3-butanediol, lactate, butene, butadiene, methyl ethyl ketone, ethylene, acetone, isopropanol, lipids, 3-hydroxypropionate, isoprene, fatty acids, 2-butanol, 1,2-propanediol, 1-propanol, monoethylene glycol, isobutene, and C6-C14 alcohols.

In at least one embodiment, the one or more fermentation product is further converted to at least one component of diesel fuel, jet fuel, gasoline, propylene, nylon 6-6, rubber, and/or resins.

In particular embodiments, at least one fermentation product is microbial biomass. In certain instances, this microbial biomass may be further processed to produce at least one component of animal feed.

DETAILED DESCRIPTION OF THE INVENTION

Figure 1:
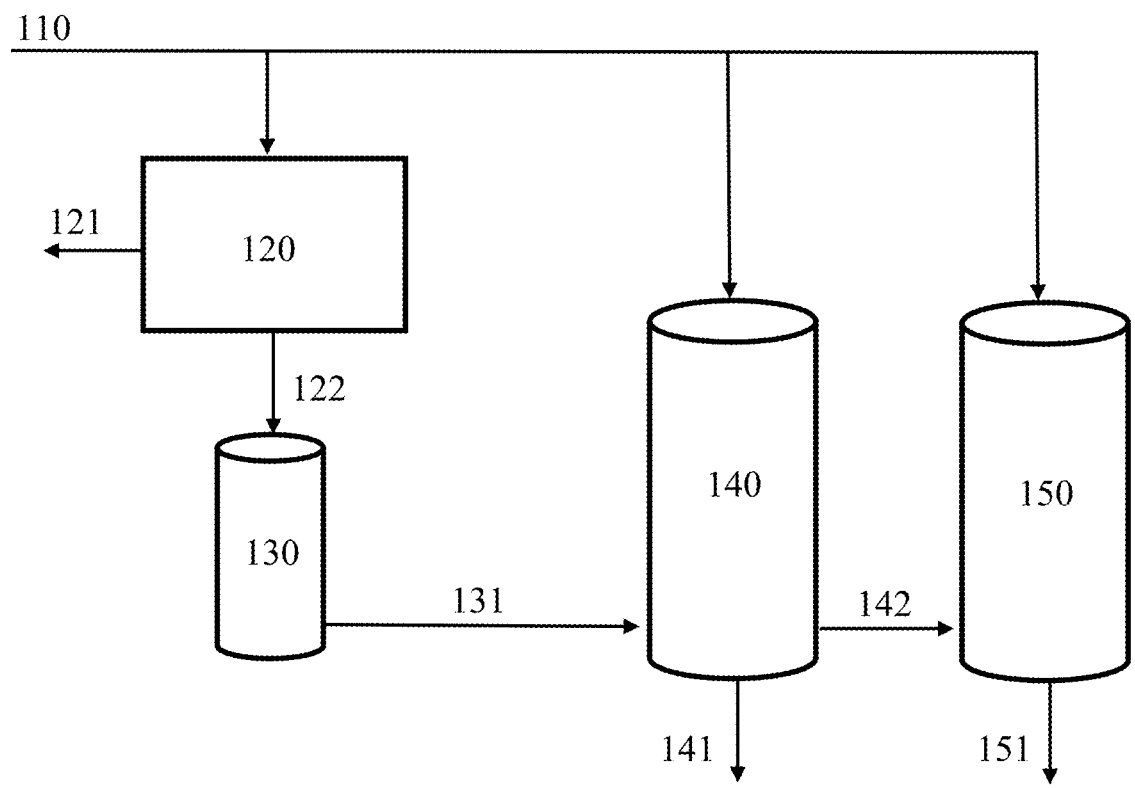
FIG. 1 is a schematic flow diagram depicting the integration of a hydrogen removal process, an inoculation reactor, and a bioreactor system.

The inventors have identified that by optimizing the composition of a gas stream being fed to the inoculation reactor, cell growth, product selectivity, and stability are optimized in both the inoculation reactor and subsequent bioreactor system. In particular, the inventors have found optimal cell growth, product selectivity, and stability when the gas stream being fed to the inoculation reactor comprises a reduced amount of hydrogen.

Definitions

Unless otherwise defined, the following terms as used throughout this specification are defined as follows:

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO or $CO_2$. A "C1-fixing microorganism" is a microorganism that has the ability to produce one or more products from a C1-carbon source. Typically, the microorganism of the invention is a C1-fixing microorganism.

"C1-containing gaseous substrates" include any gas leaving the industrial process comprising C1. In various instances, the C1-containing gaseous substrate comprises CO, $H_2$, $CO_2$, or combinations thereof. The gaseous substrate will typically contain a significant proportion of CO, preferably at least about 5% to about 100% CO by volume. The gaseous substrate may contain a significant proportion of hydrogen. For example, in particular embodiments, the substrate may comprise an approximately 2:1, or 1:1, or 1:2 ratio of $H_2$:CO. In one embodiment, the substrate comprises about 30% or less $H_2$ by volume, 20% or less $H_2$ by volume, about 15% or less $H_2$ by volume or about 10% or less $H_2$ by volume. The substrate may also contain some $CO_2$ for example, such as about 1% to about 80% $CO_2$ by volume, or 1% to about 30% $CO_2$ by volume. In one embodiment, the substrate comprises less than or equal to about 20% $CO_2$ by volume. In particular embodiments, the substrate comprises less than or equal to about 15% $CO_2$ by volume, less than or equal to about 10% $CO_2$ by volume, less than or equal to about 5% $CO_2$ by volume or substantially no $CO_2$. Additionally, the C1-containing gaseous substrate may contain one or more of oxygen ($O_2$), nitrogen ($N_2$), and/or methane ($CH_4$).

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The term "co-substrate" refers to a substance that, while not necessarily being the primary energy and material source for product synthesis, can be utilized for product synthesis when added to another substrate, such as the primary substrate.

The substrate and/or C1-carbon source may be a waste gas obtained as a by-product of an industrial process or from some other source, such as from automobile exhaust fumes or biomass gasification. In certain embodiments, the industrial process is selected from the group consisting gas emissions from carbohydrate fermentation, gas fermentation, gas emissions from cement making, pulp and paper making, steel making, oil refining and associated processes, petrochemical production, coke production, anaerobic or aerobic digestion, synthesis gas (derived from sources including but not limited to biomass, liquid waste streams, solid waste streams, municipal streams, fossil resources including natural gas, coal and oil), natural gas extraction, oil extraction, metallurgical processes, for production and/or refinement of aluminium, copper, and/or ferroalloys, geological reservoirs, and catalytic processes (derived from the steam sources including but not limited to steam methane reforming, steam naphtha reforming, petroleum coke gasification, catalyst regeneration-fluid catalyst cracking, catalyst regeneration-naphtha reforming, and dry methane reforming). In these embodiments, the substrate and/or C1-carbon source may be captured from the industrial process before it is emitted into the atmosphere, using any convenient method.

"Gas stream" refers to any stream of substrate which is capable of being passed, for example, from one module to another, from one module to a bioreactor, from one module to an inoculation reactor, from one process to another process, and/or from one module to a carbon capture means.

The term "carbon capture" as used herein refers to the sequestration of carbon compounds including $CO_2$ and/or CO from a stream comprising $CO_2$ and/or CO and either:
converting the $CO_2$ and/or CO into products; or
converting the $CO_2$ and/or CO into substances suitable for long-term storage; or
trapping the $CO_2$ and/or CO in substances suitable for long-term storage;
or a combination of these processes.

"Reactants" as used herein refer to a substance that takes part in and undergoes change during a chemical reaction. In particular embodiments, the reactants include, but are not limited to, CO and/or $H_2$.

"Hydrogen removal process" and the like includes technologies that are capable of removing and/or separating hydrogen from the C1-containing gaseous substrate. In particular embodiments, a pressure swing adsorption process and/or a membrane separation process are used as the hydrogen removal process.

The term "bioreactor" "bioreactor system" and the like includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR) or other vessel or other device suitable for gas-liquid contact. The bioreactor is preferably adapted to receive a gaseous substrate comprising CO or $CO_2$ or $H_2$ or mixtures thereof. The bioreactor may comprise multiple reactors (stages), either in parallel or in series. Preferably, the bioreactor is configured to receive an inoculum from an invocation reactor. Preferably, the bioreactor is configured as a production reactor, where most of the fermentation products are produced.

The term "inoculation reactor", "inoculator", "seed reactor" and the like includes a fermentation device for establishing and promoting cell growth. The inoculation reactor is preferably adapted to receive a gaseous substrate comprising CO or $CO_2$ or $H_2$ or mixtures thereof. Preferably, the inoculation reactor is a reactor where cell growth is first initiated. In various embodiments, the inoculation reactor is where previously growth cells are revived. In the various embodiments, the inoculator initiates cell growth of one or more microorganism to produce an inoculum, which may then be transferred to the bioreactor system where each bioreactor is configured to promote the production of one or more fermentation product. In certain instances, the inoculator has a reduced volume when compared to the subsequent one or more bioreactor.

"Nutrient media" or "Nutrient medium" is used to describe bacterial growth media. Generally, this term refers to a media containing nutrients and other components appropriate for the growth of a microbial culture. The term "nutrient" includes any substance that may be utilized in a metabolic pathway of a microorganism. Exemplary nutrients include potassium, B vitamins, trace metals, and amino acids.

The term "fermentation broth" or "broth" is intended to encompass the mixture of components including nutrient media and a culture or one or more microorganisms. It should be noted that the term microorganism and the term bacteria are used interchangeably throughout the document.

The term "inoculum" is intended to encompass the fermentation broth initially grown in the inoculation reactor which is then passed to the one or more subsequent bioreactors to seed the one or more subsequent bioreactor. Preferably, the inoculum is utilized by the one or more bioreactors to produce one or more fermentation product.

The term "desired composition" is used to refer to the desired level and types of components in a substance, such as, for example, of a gas stream. More particularly, a gas is considered to have a "desired composition" if it contains a particular component (e.g. CO, $H_2$, and/or $CO_2$) and/or contains a particular component at a particular proportion and/or does not contain a particular component (e.g. a constituent harmful to the microorganisms) and/or does not contain a particular component at a particular proportion. More than one component may be considered when determining whether a gas stream has the desired composition. In one or more embodiment, the "desired composition" of the C1-containing gaseous substrate is defined in terms of an $H_2$:CO molar ratio. In various embodiments, the desired composition of the C1-containing gaseous substrate being passed to the inoculation reactor differs from the desired composition of the C1-containing gaseous substrate being passed to the bioreactor system.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

Unless the context requires otherwise, the phrases "fermenting", "fermentation process" or "fermentation reaction" and the like, as used herein, are intended to encompass both the growth phase and product biosynthesis phase of the gaseous substrate.

A "microorganism" is a microscopic organism, especially a bacterium, archea, virus, or fungus. The microorganism of the invention is typically a bacterium. As used herein, recitation of "microorganism" should be taken to encompass "bacterium."

A "parental microorganism" is a microorganism used to generate a microorganism of the invention. The parental microorganism may be a naturally-occurring microorganism (e.g., a wild-type microorganism) or a microorganism that has been previously modified (e.g., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited on Jun. 7, 2010, with Deutsche Sammlung von Mikroorganismen and Zellkulturen GmbH (DSMZ) located at Inhoffenstraß 7B, D-38124 Braunschweig, Germany on Jun. 7, 2010, under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *Clostridium autoethanogenum*, *Clostridium ljungdahlii*, or *Clostridium ragsdalei*. In a preferred embodiment, the microorganism of the invention is derived from *Clostridium autoethanogenum* LZ1561, which is deposited under DSMZ accession number DSM23693.

"Wood-Ljungdahl" refers to the Wood-Ljungdahl pathway of carbon fixation as described, i.e., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, the microorganism of the invention contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5 vol. % oxygen). Typically, the microorganism of the invention is an anaerobe.

"Acetogens" are obligately anaerobic bacteria that use the Wood-Ljungdahl pathway as their main mechanism for energy conservation and for the synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. Typically, the microorganism of the invention is an acetogen.

An "ethanologen" is a microorganism that produces or is capable of producing ethanol. Typically, the microorganism of the invention is an ethanologen.

An "autotroph" is a microorganism capable of growing in the absence of organic carbon. Instead, autotrophs use inorganic carbon sources, such as CO and/or $CO_2$. Typically, the microorganism of the invention is an autotroph.

A "carboxydotroph" is a microorganism capable of utilizing CO as a sole source of carbon and energy. Typically, the microorganism of the invention is a carboxydotroph.

The microorganism of the invention may be cultured with the gas stream to produce one or more products. For instance, the microorganism of the invention may produce or may be engineered to produce ethanol (WO 2007/117157), acetate (WO 2007/117157), butanol (WO 2008/115080 and WO 2012/053905), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2014/0369152), chorismate-derived products (WO 2016/191625), 3-hydroxybutyrate (WO 2017/066498), and 1,3-butanediol (WO 2017/0066498). In addition to one or more target products, the microorganism of the invention may also produce ethanol, acetate, and/or 2,3-butanediol. In certain embodiments, microbial biomass itself may be considered a product. These products may be further converted to produce at least one component of diesel, jet fuel, and/or gasoline. Additionally, the microbial biomass may be further processed to produce a single cell protein (SCP).

A "single cell protein" (SCP) refers to a microbial biomass that may be used in protein-rich human and/or animal feeds, often replacing conventional sources of protein supplementation such as soymeal or fishmeal. To produce a single cell protein or other product, the process may comprise additional separation, processing, or treatments steps. For example, the method may comprise sterilizing the microbial biomass, centrifuging the microbial biomass, and/or drying the microbial biomass. In certain embodiments, the microbial biomass is dried using spray drying or paddle drying. The method may also comprise reducing the nucleic acid content of the microbial biomass using any method known in the art, since intake of a diet high in nucleic acid content may result in the accumulation of nucleic acid degradation products and/or gastrointestinal distress. The single cell protein may be suitable for feeding to animals, such as livestock or pets. In particular, the animal feed may be suitable for feeding to one or more beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents. The composition of the animal feed may be tailored to the nutritional requirements of different animals. Furthermore, the process may comprise blending or combining the microbial biomass with one or more excipients.

An "excipient" may refer to any substance that may be added to the microbial biomass to enhance or alter the form, properties, or nutritional content of the animal feed. For example, the excipient may comprise one or more of a carbohydrate, fiber, fat, protein, vitamin, mineral, water, flavor, sweetener, antioxidant, enzyme, preservative, probiotic, or antibiotic. In some embodiments, the excipient may be hay, straw, silage, grains, oils or fats, or other plant material. The excipient may be any feed ingredient identified in Chiba, Section 18: Diet Formulation and Common Feed Ingredients, Animal Nutrition Handbook, $3^{rd}$ revision, pages 575-633, 2014.

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism but is not produced by a genetically unmodified microorganism from which the genetically modified microorganism is derived.

"Selectivity" refers to the ratio of the production of a target product to the production of all fermentation products produced by a microorganism. The microorganism of the invention may be engineered to produce products at a certain selectivity or at a minimum selectivity. In one embodiment, a target product account for at least about 5 wt. %, 10 wt. %, 15 wt. %, 20 wt. %, 30 wt. %, 50 wt. %, 75 wt. %, or 90 wt. % of all fermentation products produced by the microorganism of the invention. In one embodiment, the target product accounts for at least 10 wt. % of all fermentation products produced by the microorganism of the invention, such that the microorganism of the invention has a selectivity for the target product of at least 10 wt. %. In another embodiment, the target product accounts for at least 30 wt. % of all fermentation products produced by the microorganism of the invention, such that the microorganism of the invention has a selectivity for the target product of at least 30 wt. %. In one embodiment, the target product accounts for at least 90 wt. % of all fermentation products produced by the microorganisms, such that the microorganism of the invention has a selectivity for the target product of at least 90 wt. %.

Target products may be separated or purified from a fermentation broth using any method or combination of methods known in the art, including, for example, fractional distillation, evaporation, pervaporation, gas stripping, phase separation, and extractive fermentation, including, for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time, in turn, dictates the required volume of a bioreactor, the use of pressurized systems can greatly reduce the volume of the bioreactor required, and consequently the capital cost of the fermentation equipment.

Description

Controlling the composition of the C1-containing gaseous substrate being fed to an inoculator and/or a bioreactor has been found particularly useful for promoting cell growth, product selectivity, and stability both in the inoculation reactor and subsequent bioreactors. Preferably, the C1-containing substrate is composition controlled before being fed to an inoculation reactor, to produce an inoculum for feeding one or more downstream reactors. Preferably, the inoculation reactor comprises a culture of one or more C1-fixing microorganism in a liquid nutrient medium and is capable of receiving the composition controlled C1-containing gaseous substrate to produce an inoculum through fermentation.

The inventors have found that when a C1-containing gaseous substrate that is rich in hydrogen is used for fermentation, the fermentation process often lacks long-term product selectivity and stability. Surprisingly, the inventors have found that when operating a fermentation process under hydrogen-rich conditions, providing an alternate carbon monoxide (CO) rich C1-containing stream to the inoculation reactor, results in not only an increase in biomass growth and biomass growth rate, but also results in increased selectivity to ethanol and improved stability in the downstream bioreactors.

This invention has particular applicability to fermentation processes utilizing industrial gas streams comprising $H_2$ at a $H_2$:CO molar ratio of at least 3:1, however it is considered that the invention is also beneficial to industrial streams comprising lower $H_2$ compositions such as gas streams having $H_2$:CO molar ratios of 2:1 or 1.5:1, or 1.1:1. In one embodiment, the invention provides a process for producing one or more fermentation product, the process comprising: (a) passing at least a portion of a C1-containing gaseous substrate to an inoculation reactor and at least a portion of the C1-containing gaseous substrate to a bioreactor; (b) fermenting the C1-containing gaseous substrate in the inoculation reactor to produce an inoculum; (c) passing at least a portion of the inoculum to at least one bioreactor; and (d) fermenting the C1-containing gaseous substrate in the bioreactor to produce at least one fermentation product; wherein the C1-containing gaseous substrate being passed to the inoculation reactor is subjected to at least one $H_2$ removal process prior to being passed to the inoculation reactor.

In particular embodiments, the bioreactor comprises one or more primary reactors linked to one or more secondary reactors. In certain embodiments, the primary reactor(s) operates at conditions to promote biomass production, and the secondary reactor(s) operates at conditions to promote metabolite production. In various embodiments, the $H_2$ rich C1-containing gaseous substrate provided to the primary and secondary reactors is from the same industrial source and has substantially the same composition.

In one embodiment, the CO-rich C1-containing gaseous substrate, and the $H_2$ rich C1-containing gaseous substrate are derived from the same industrial source. In various embodiments, at least a portion of an $H_2$ rich C1-containing gaseous substrate is passed to a hydrogen removal process, prior to being provided to the inoculation reactor, the hydrogen removal process being configured to separate at least a portion of hydrogen from the $H_2$ rich C1-containing gaseous substrate to produce the CO-rich C1-containing gaseous substrate. In particular embodiments, the treatment zone comprises an $H_2$ membrane separation module and/or a pressure swing adsorption (PSA) process. Preferably, the hydrogen removal process comprises a membrane separation module.

In one or more embodiment, the $H_2$ rich C1-containing gaseous substrate is derived from an industrial process.

In alternative embodiments, the CO-rich C1-containing gaseous substrate comprises a bottled CO gas stream. In one embodiment, the bottled CO gas is blended with one or more gaseous components such as nitrogen and/or carbon dioxide. In further embodiments, the CO-rich C1-containing gaseous substrate is a CO-rich gaseous stream derived from a different source than the $H_2$ rich C1-containing gaseous substrate. In one embodiment, the CO-rich C1-containing gaseous substrate is derived from a $CO_2$ electrolysis process.

Hydrogen Separation

The volume of gas necessary may, in some instances, make using bottled gas prohibitive due to cost. Therefore, it is preferred that the $H_2$ rich C1-containing gaseous substrate is treated to remove at least a portion of hydrogen from the substrate and produce a CO-rich C1-containing gaseous substrate. Suitable methods for treating an $H_2$ rich C1-containing gaseous substrate may include but are not limited to, membrane separation technologies, and pressure swing adsorption technologies.

Membrane separation modules provide a low cost, relatively simple way to remove at least a portion of hydrogen from a gaseous substrate. For example, a reformer syngas with the composition of 72 vol. % $H_2$, 14 vol. % CO, 7 vol. % $CO_2$ and 7 vol. % $CH_4$ at 25 bara pressure passing through a demonstrative membrane separation module results in a high-pressure CO-rich stream and a low-pressure $H_2$ rich stream. The high-pressure CO-rich stream remains at 25 bara and contains 50 vol. % CO, 16 vol. % $H_2$, 25 vol. % $CH_4$, and 9 vol. % $CO_2$. The low-pressure $H_2$ rich stream is reduced to 1 bara and contains 92 vol. % $H_2$, 6 vol. % $CO_2$, and 1 vol. % each of CO and $CH_4$. The high-pressure CO-rich stream can be provided to the inoculator as a CO-rich C1-containing gaseous substrate. The high-pressure CO-rich stream provides the added benefit of not requiring further compression, thus avoiding the capital cost associated with an addition compressor unit for the inoculation reactor.

Pressure swing adsorption process technologies are a more complicated yet effective way to remove at least a portion of hydrogen from a gaseous substrate. When utilizing a pressure swing adsorption process, the resulting CO-rich stream is low pressure. While the use of a pressure swing adsorption process is feasible, the CO-rich C1-containing gaseous substrate may need to be compressed prior to being provided to the inoculation reactor or any bioreactor, thereby increasing the capital cost associated with the inoculation reactor. This may be at least partially offset, however, when considering the fact that the hydrogen stream produced by the pressure swing adsorption process is at high pressure and can be sold as a product.

$CO_2$ Electrolysis

An alternative method for providing a CO-rich C1-containing gaseous substrate is through use of $CO_2$ electrolysis. $CO_2$ electrolysis processes convert a $CO_2$ feedstock to CO and $O_2$. The use of a $CO_2$ electrolysis process to provide a CO-rich stream for the inoculator may be of interest at industrial sites comprising a $CO_2$ rich stream in addition to an $O_2$ rich stream. Additionally, it is further considered that the tail gas from the inoculation reactor and/or the bioreactor system, being rich in $CO_2$ can be used as a feedstock for the $CO_2$ electrolysis units.

FIG. 1 shows a schematic flow diagram of one embodiment of the invention. A portion of a C1-containing gaseous substrate is passed via piping means 110 to an inoculation reactor 130 where the C1-containing substrate is fermented to produce an inoculum. At least a portion of the inoculum is passed via piping means 131 to the bioreactor system 140,150 where a portion of the C1-containing gaseous substrate is also passed via piping means 110 to be fermented to produce at least one product 141, 151. The C1-containing gaseous substrate being passed to the inoculation reactor 130 is subjected to at least one hydrogen removal process 120 before being sent to the inoculation reactor 130. The hydrogen removal process 120 receives the C1-containing gaseous substrate via piping means 110 and removes at least a portion of the hydrogen 121 from the C1-containing gaseous substrate to produce a CO-rich C1-containing gaseous substrate, which is fed to the inoculation reactor 130 via piping means 122.

Preferably, the C1-containing gaseous substrate being passed to the inoculation reactor 130 comprises $H_2$ at an $H_2$:CO molar ratio of less than 1:1. In certain embodiments the C1-containing gaseous substrate being passed to the inoculation reactor 130 comprises $H_2$ at an $H_2$:CO molar ratio of less than 0.8:1. Preferably, the C1-containing gaseous substrate being passed to the inoculation reactor 130 comprises $H_2$ at an $H_2$:CO molar ratio between 0.02:1 to 1:1. In various instances, the hydrogen removal process 120 removes at least a portion of hydrogen through use of at least one membrane separation module. In various instances, the hydrogen removal process 120 removes at least a portion of hydrogen through use of at least one pressure swing adsorption process. In various embodiments, the hydrogen removal process 120 removes at least a portion of hydrogen through use of both a membrane separation module and a pressure swing adsorption process.

In certain instances, the C1-containing gaseous substrate being fed to the inoculation reactor 130 and the bioreactor system 140, 150 is derived at least in part from an industrial source. Preferably, the industrial source is selected from the group consisting of carbohydrate fermentation, gas fermentation, cement making, pulp and paper making, steel making, oil refining and associated processes, petrochemical production, coke production, anaerobic or aerobic digestion, synthesis gas, natural gas extraction, oil extraction, metallurgical processes, for production and/or refinement of aluminium, copper, and/or ferroalloys, geological reservoirs, and catalytic processes.

Preferably, the fermentation product 141, 151 produced by the bioreactor system 140, 150 is selected from the group consisting of: ethanol, acetate, butanol, butyrate, 2,3-butanediol, 1,3-butanediol, lactate, butene, butadiene, methyl ethyl ketone, ethylene, acetone, isopropanol, lipids, 3-hydroxypropionate, isoprene, fatty acids, 2-butanol, 1,2-propanediol, 1-propanol, monoethylene glycol, isobutene, and C6-C14 alcohols. In various instances, at least a portion of the product 141, 151 is further converted to at least one component of diesel fuel, jet fuel, gasoline, propylene, nylon 6-6, rubber, and/or resins. In various instances, at least one fermentation product 141, 151 is microbial biomass. This microbial biomass may, in some instances, be further processed to produce at least one component of animal feed.

In various embodiments, the fermentation broth from one bioreactor 140 may be passed to another bioreactor 150 within the bioreactor system 140,150 via piping means 142.

Figure 2:
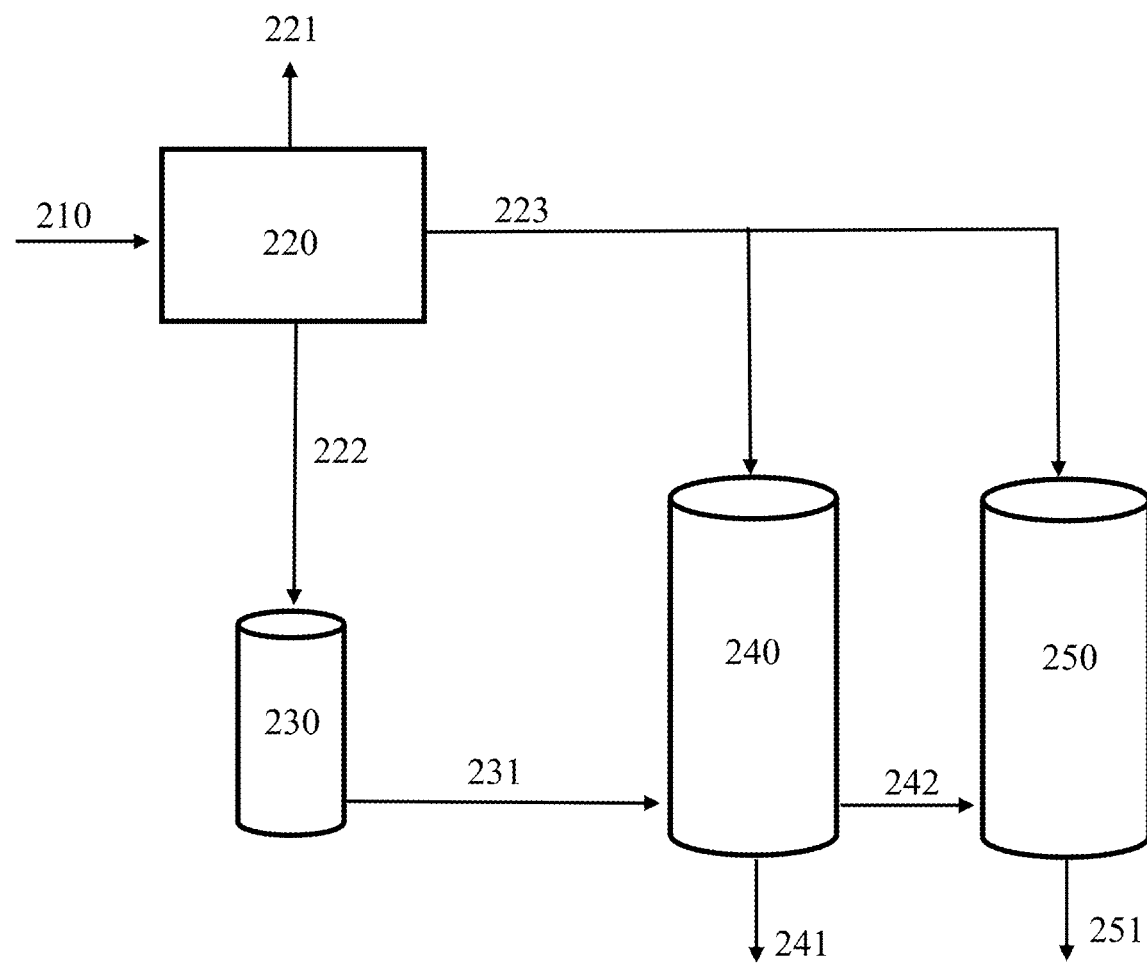
FIG. 2 is a schematic flow diagram depicting the integration of a hydrogen removal process, an inoculation reactor, and a bioreactor system, where the hydrogen removal process is upstream of both the inoculation reactor and the bioreactor system, in accordance with one aspect of the invention.

FIG. 2 shows a schematic flow diagram of one embodiment of the invention. A portion of a C1-containing gaseous substrate is passed via piping means 210 to an inoculation reactor 230 where the C1-containing substrate is fermented to produce an inoculum. At least a portion of the inoculum is passed via piping means 231 to the bioreactor system 240,250 where a portion of the C1-containing gaseous substrate is also passed via piping means 210 to be fermented to produce at least one product 241, 251. The C1-containing gaseous substrate being passed to the inoculation reactor 230 and the bioreactor system 140,150 is subjected to at least one hydrogen removal process 220 before being sent to the inoculation reactor 230. The hydrogen removal process 220 receives the C1-containing gaseous substrate via piping means 210 and removes at least a portion of the hydrogen 221 from the C1-containing gaseous substrate to produce a CO-rich C1-containing gaseous substrate, which is fed to the inoculation reactor 230 via piping means 222 and to the bioreactor system, 140,150 via piping means 223.

Preferably, the C1-containing gaseous substrate being passed to the inoculation reactor 230 and the bioreactor system 240,250 comprises $H_2$ at an $H_2$:CO molar ratio of less than 1:1. In certain embodiments the C1-containing gaseous substrate being passed to the inoculation reactor 230 and the bioreactor system 240,250 comprises $H_2$ at an $H_2$:CO molar ratio of less than 0.8:1. Preferably, the C1-containing gaseous substrate being passed to the inoculation reactor 230 and the bioreactor system 240,250 comprises $H_2$ at an $H_2$:CO molar ratio between 0.02:1 to 1:1. In various instances, the hydrogen removal process 220 removes at least a portion of hydrogen through use of at least one membrane separation module. In various instances, the hydrogen removal process 220 removes at least a portion of hydrogen through use of at least one pressure swing adsorption process. In various embodiments, the hydrogen removal process 220 removes at least a portion of hydrogen through use of both a membrane separation module and a pressure swing adsorption process.

In certain instances, the C1-containing gaseous substrate being fed to the inoculation reactor 230 and the bioreactor system 240, 250 is derived at least in part from an industrial source. Preferably, the industrial source is selected from the group consisting of carbohydrate fermentation, gas fermentation, cement making, pulp and paper making, steel making, oil refining and associated processes, petrochemical production, coke production, anaerobic or aerobic digestion, synthesis gas, natural gas extraction, oil extraction, metallurgical processes, for production and/or refinement of aluminium, copper, and/or ferroalloys, geological reservoirs, and catalytic processes.

Preferably, the fermentation product 241, 251 produced by the bioreactor system 240, 250 is selected from the group consisting of: ethanol, acetate, butanol, butyrate, 2,3-butanediol, 1,3-butanediol, lactate, butene, butadiene, methyl ethyl ketone, ethylene, acetone, isopropanol, lipids, 3-hydroxypropionate, isoprene, fatty acids, 2-butanol, 1,2-propanediol, 1-propanol, monoethylene glycol, isobutene, and C6-C14 alcohols. In various instances, at least a portion of the product 241, 251 is further converted to at least one component of diesel fuel, jet fuel, gasoline, propylene, nylon 6-6, rubber, and/or resins. In various instances, at least one fermentation product 241, 251 is microbial biomass. This microbial biomass may, in some instances, be further processed to produce at least one component of animal feed.

In various embodiments, the fermentation broth from one bioreactor 240 may be passed to another bioreactor 250 within the bioreactor system 240,250 via piping means 242.

Figure 3:
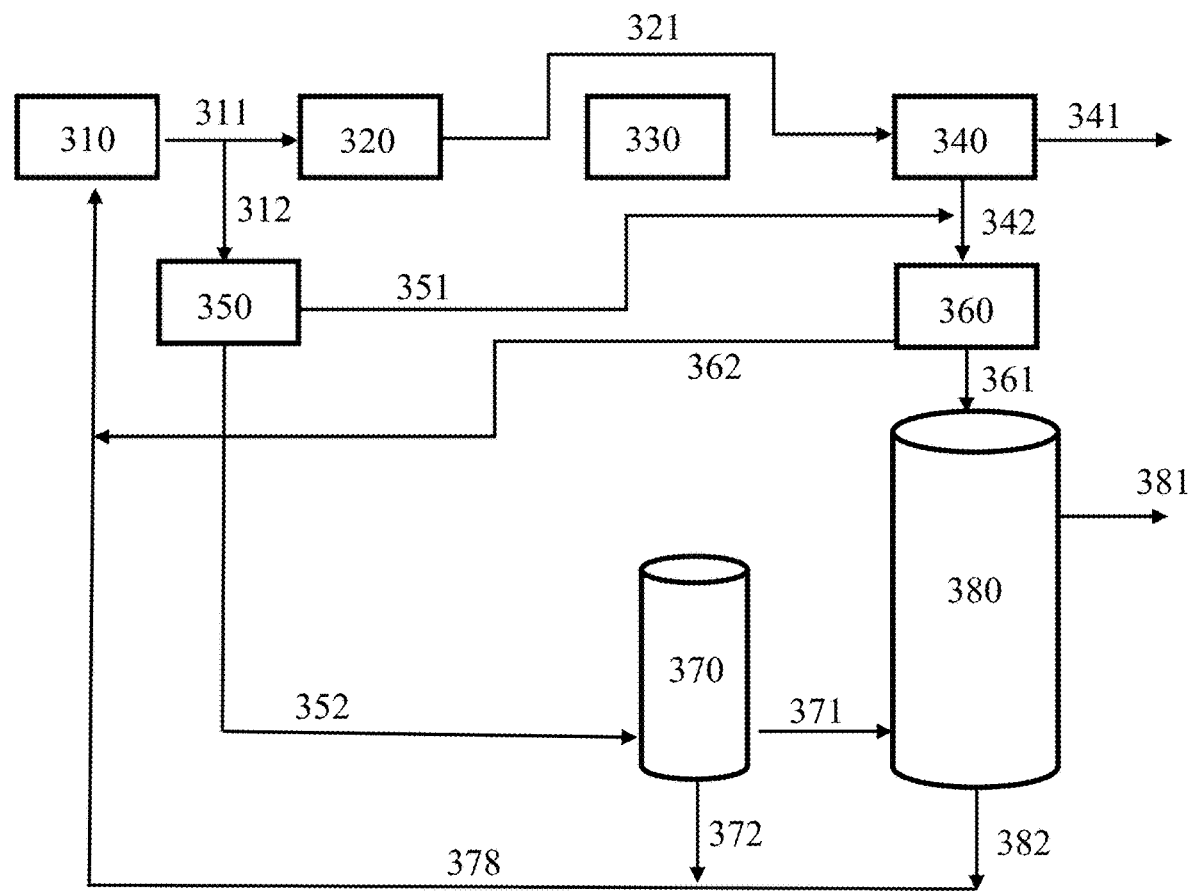
FIG. 3 is a schematic flow diagram further depicting two water-gas-shift processes and a pressure swing adsorption process upstream of the bioreactor system, where one water-gas-shift process is bypassed, in accordance with one aspect of the invention.
Figure 4:
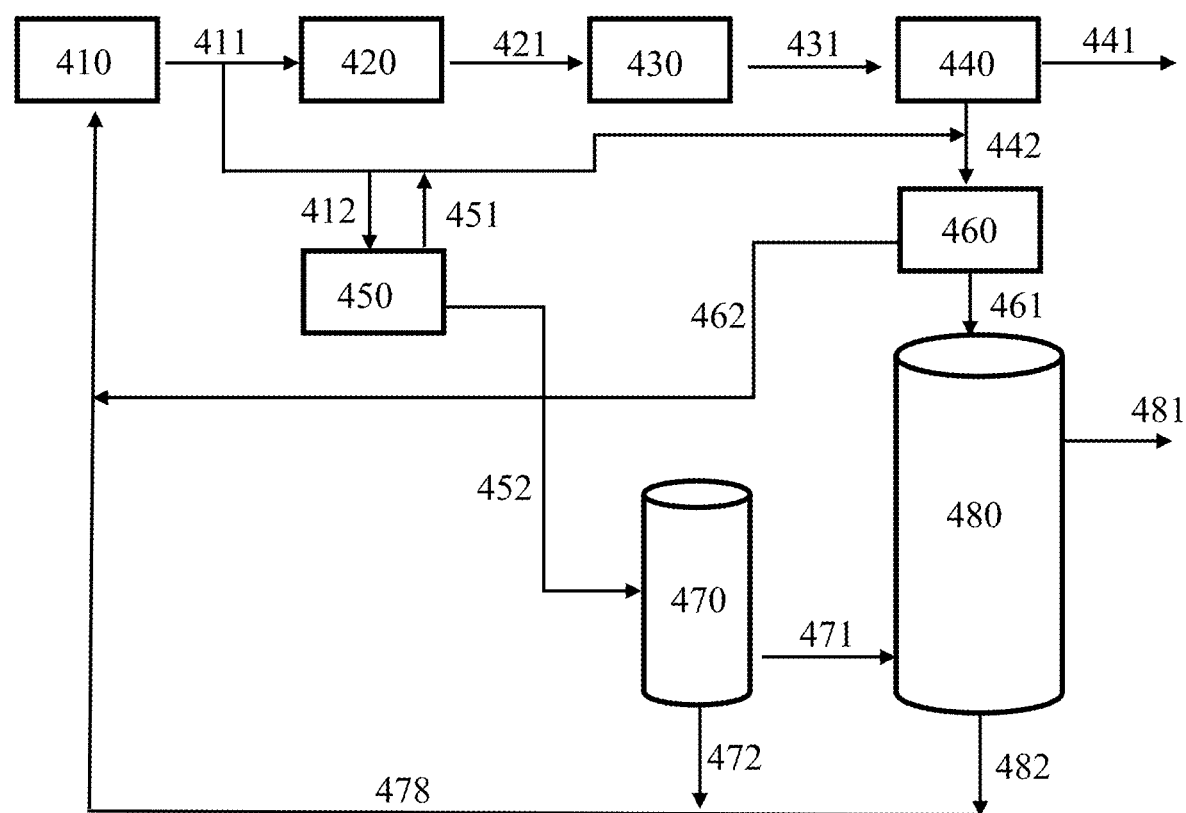
FIG. 4 is a schematic flow diagram further depicting two water-gas-shift processes and a pressure swing adsorption process upstream of the bioreactor system, in accordance with one aspect of the invention.
Figure 5:
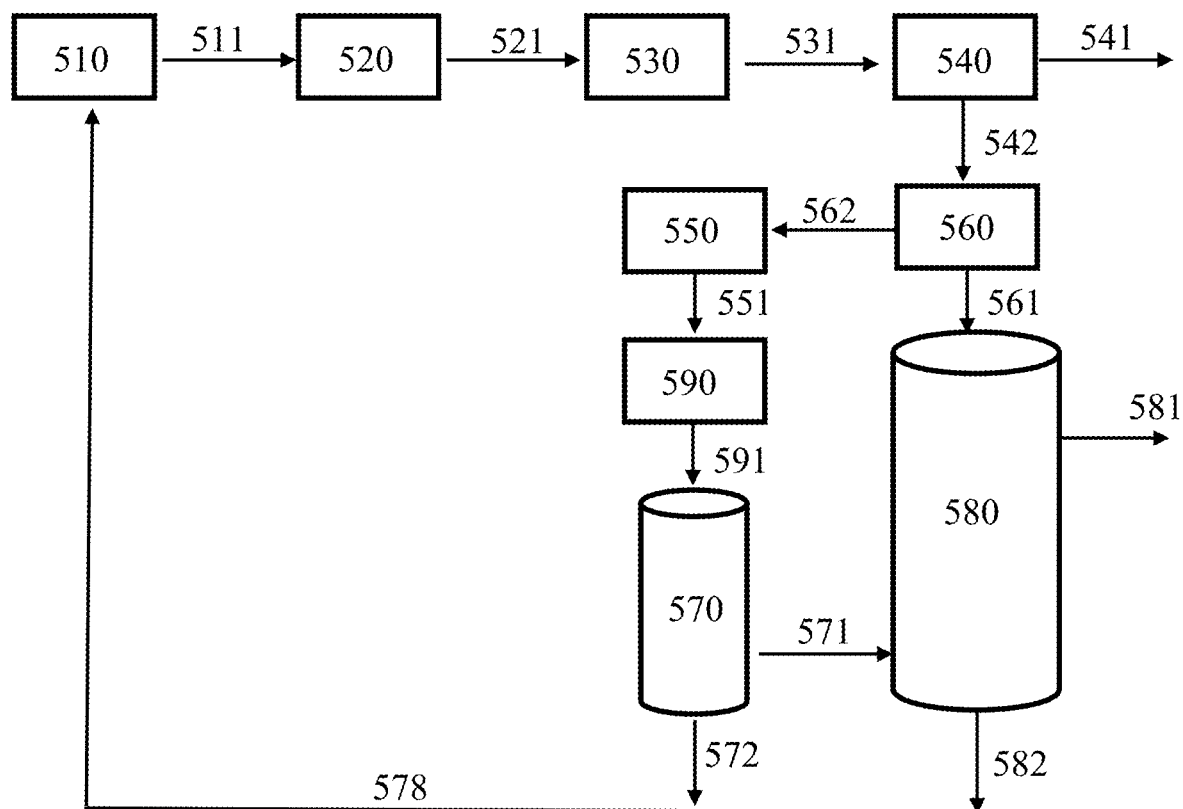
FIG. 5 is a schematic flow diagram further depicting additional hydrogen removal processes upstream of the inoculation reactor, in accordance with one aspect of the invention.

FIGS. 3, 4 and 5 depict various embodiments of the invention, using a hydrogen production process of a refining operation as the industrial source of the $H_2$ rich C1-containing gaseous substrate. A typical hydrogen production process, as depicted in FIG. 3, FIG. 4 and FIG. 5, contains the following stages: (i) a reforming process wherein a $CH_4$ containing feedstock is converted to a syngas stream comprising CO and $H_2$; (ii) at least one water gas shift step, wherein a portion of the CO is reacted with water to produce $H_2$ and $CO_2$; and (iii) a pressure swing adsorption (PSA) module adapted to recover hydrogen from the gas stream.

FIG. 3 shows one embodiment of the invention utilizing an $H_2$ rich C1-containing gaseous substrate from a reforming process 310. At least a portion of the $H_2$ rich C1-containing gaseous substrate is flowed to a membrane separation module 350 via piping means 312. The membrane separation module 350 separates the C1-containing gaseous substrate into a high-pressure CO-rich stream, and a low pressure $H_2$ rich stream. At least a portion of the low-pressure CO-rich stream is passed to an inoculation reactor 370 via piping means 352. At least a portion of the low-pressure $H_2$ rich stream is passed to a pressure swing adsorption process 360 via piping means 351. In at least one embodiment, the gaseous substrate is passed to a compressor prior to being passed to the pressure swing adsorption process 360. In one embodiment, the CO-rich stream comprises at least 40% CO, or at least 50% CO, or at least 60% CO. In one embodiment the pressure of the CO-rich C1-containing stream is at least 15 bar, or at least 20 bar, or at least 25 bar.

In various embodiments, the process may include multiple water gas shift processes 320, 330 and/or multiple hydrogen removal processes 350, 340, 360. As shown in FIG. 3, the C1-containing gaseous substrate may first be passed from a reforming process 310 to a water gas shift process 320 via piping means 311 to convert at least a portion of the $CH_4$ to a syngas stream comprising CO and $H_2$. This gas stream may optionally bypass one or more further water gas shift process 330 via piping means 321 and be fed to the one or more hydrogen removal process 340 to separate at least a portion of the hydrogen 341 from the gas stream. This stream may then be passed to one or more further hydrogen removal process 360 via piping means 342. The stream from the one or more further hydrogen removal process 360 may be sent to the bioreactor 380 via piping means 361 for fermentation. At least a portion of the substrate not sent to the bioreactor may optionally be sent to the reforming process 310 via piping means 362. In various instances, the bioreactor 380 receives the gaseous substrate and produces one or more fermentation product 381. Optionally, the tail gas from both the inoculation reactor 370 and the bioreactor 380 can be passed back to the reforming process 310 via separate piping means 372, 382 and/or a blended stream 378.

In the various embodiments, the inoculation reactor 370 and the bioreactor 380 are configured in a step-wise manner, whereby the inoculation reactor 370 ferments a CO-rich C1-containing gaseous substrate to produce an inoculum, which is then fed to the bioreactor 380 via piping means 371. By utilizing this inoculum in the bioreactor 380, product selectivity and stability of the fermentation process is improved.

In another embodiment, as shown in FIG. 4, an $H_2$ rich C1-containing stream from a reforming process 410 is flowed to pressure swing adsorption process 450 via piping means 412 provided upstream of the inoculation reactor 470. The pressure swing adsorption process 450 separates the C1-containing stream into a high-pressure $H_2$ rich stream and a low-pressure CO-rich stream. The low-pressure CO-rich stream may be passed to a compressor prior to being passed to the inoculation reactor 470 via piping means 452. In one embodiment, the CO-rich stream being passed to the inoculation reactor 470 comprises at least 30% CO or at least 40% CO, or at least 50% CO, or at least 60% CO. The separated hydrogen may be passed from the pressure swing adsorption process 450 to another pressure swing adsorption process 460 via piping means 451. In various embodiments, the process may include multiple water gas shift processes 420, 430 and/or multiple hydrogen removal processes 450, 440, 460.

As shown in FIG. 4, the C1-containing gaseous substrate may first be passed from a reforming process 410 to a water gas shift process 420 via piping means 411 to convert at least a portion of the $CH_4$ to a syngas stream comprising CO and $H_2$. This gas stream may then be passed to one or more further water gas shift process 430 via piping means 421 and be fed to the one or more hydrogen removal process 440 via piping means 431 to separate at least a portion of the hydrogen 441 from the gas stream. This stream may then be passed to one or more further hydrogen removal process 460 via piping means 442. The stream from the one or more further hydrogen removal process 460 may be sent to the bioreactor 480 via piping means 461 for fermentation. At least a portion of the substrate not sent to the bioreactor may optionally be sent to the reforming process 410 via piping means 462. In various instances, the bioreactor 480 receives the gaseous substrate and produces one or more fermentation product 481. Optionally, the tail gas from both the inoculation reactor 470 and the bioreactor 480 can be passed back to the reforming process 410 via separate piping means 472, 482 and/or a blended stream 478.

In the various embodiments, the inoculation reactor 470 and the bioreactor 480 are configured in a step-wise manner, whereby the inoculation reactor 470 ferments a CO-rich C1-containing gaseous substrate to produce an inoculum, which is then fed to the bioreactor 480 via piping means 471. By utilizing this inoculum in the bioreactor 480, product selectivity and stability of the fermentation process is improved.

In another embodiment, as shown in FIG. 5, the C1-containing stream from the reforming process 510 may be sent to multiple hydrogen removal processes 540, 550, 560, 590 before being sent to either the inoculation reactor 570 and/or the bioreactor 580. In various instances, the C1-containing stream may be sent to a compressor before and/or between a hydrogen removal process. By sending the C1-containing stream to multiple hydrogen removal processes the CO composition in the C1-containing stream may be further enriched.

In various embodiments, the process may include multiple water gas shift processes 520, 530 in combination with multiple hydrogen removal processes 540, 550, 560. As shown in FIG. 5, the C1-containing gaseous substrate may first be passed from a reforming process 510 to a water gas shift process 520 via piping means 511 to convert at least a portion of the $CH_4$ to a syngas stream comprising CO and $H_2$. This gas stream may then be passed to one or more further water gas shift process 530 via piping means 521 and be fed to the one or more hydrogen removal process 540 via piping means 531 to separate at least a portion of the hydrogen 541 from the gas stream. This stream may then be passed to one or more further hydrogen removal process 560 via piping means 542. The stream from the one or more further hydrogen removal process 560 may be sent to the bioreactor 580 via piping means 561 for fermentation. At least a portion of the substrate not sent to the bioreactor may optionally be sent to a subsequent hydrogen removal process 550 via piping means 562 and optionally a further hydrogen removal process 590 via piping means 551, which ultimately may be sent to the inoculation reactor 570, via piping means 591, to produce an inoculum.

In various instances, the bioreactor 580 receives the gaseous substrate and produces one or more fermentation product 581. Optionally, the tail gas from both the inoculation reactor 570 and the bioreactor 580 can be passed back to the reforming process 510 via separate piping means 572, 582 and/or a blended stream 578.

In the various embodiments, the inoculation reactor 570 and the bioreactor 580 are configured in a step-wise manner, whereby the inoculation reactor 570 ferments a CO-rich C1-containing gaseous substrate to produce an inoculum, which is then fed to the bioreactor 580 via piping means 571. By utilizing this inoculum in the bioreactor 580, product selectivity and stability of the fermentation process is improved.

It is to be understood, that whilst FIG. 3, FIG. 4 and FIG. 5 are representations of an integration with a hydrogen production process the current application is not to be limited to integration with a hydrogen production process.

EXAMPLES

The following examples further illustrate the invention but, of course, should not be construed to limit its scope in any way.

Example 1

Figure 6A:
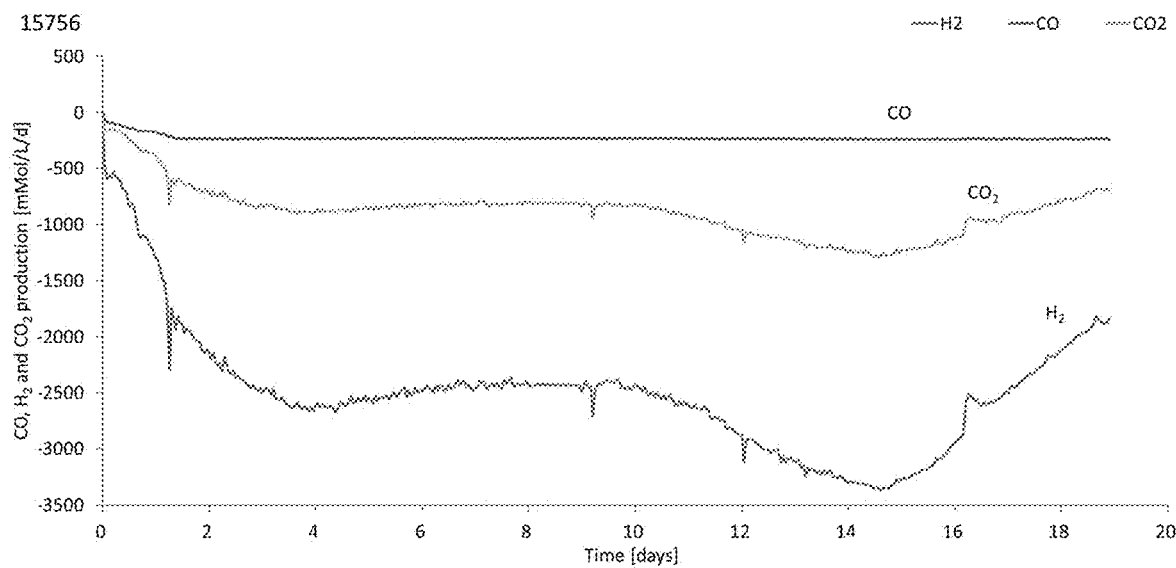
FIGS. 6a and 6b are graphs showing metabolite production and gas uptake in a first bioreactor according to Example 1.
Figure 6B:
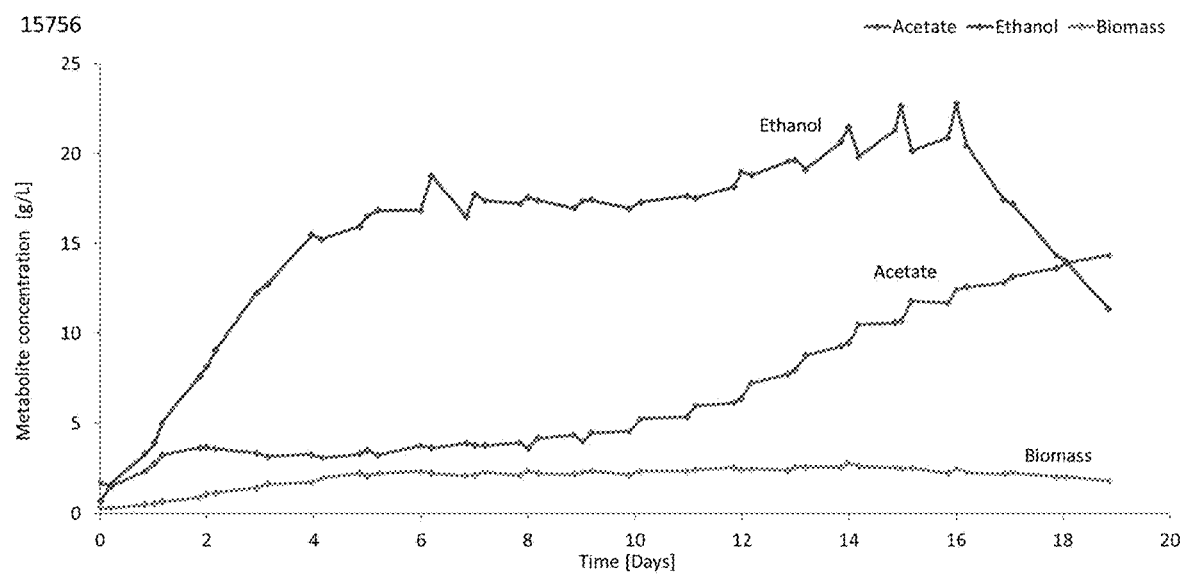
Figure 7A:
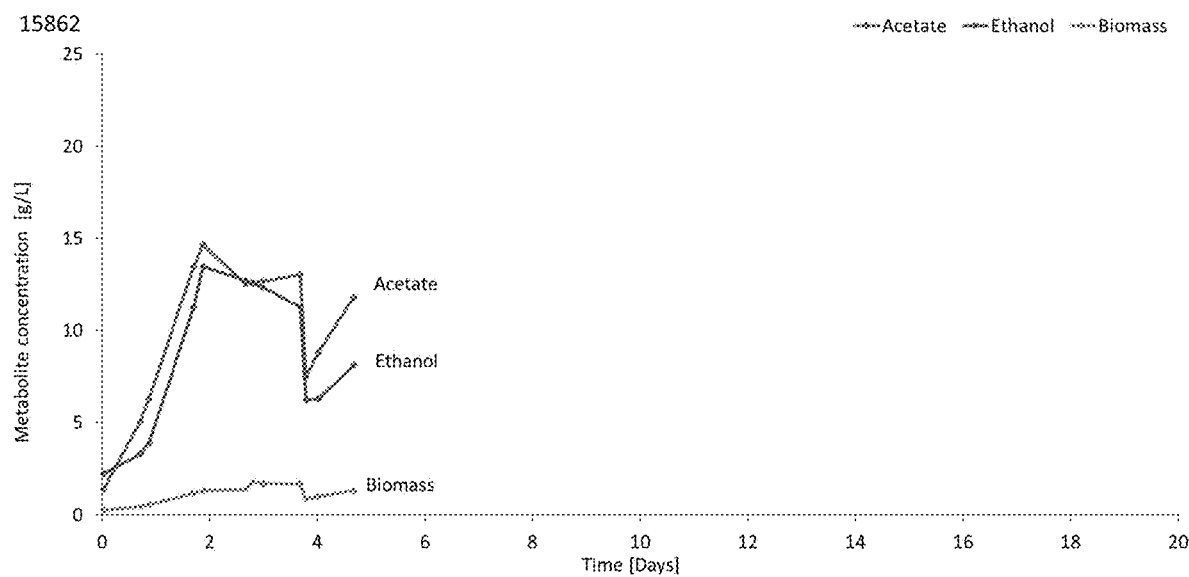
FIGS. 7a and 7b are graphs showing metabolite production and gas uptake in a second bioreactor according to Example 1.
Figure 7B:
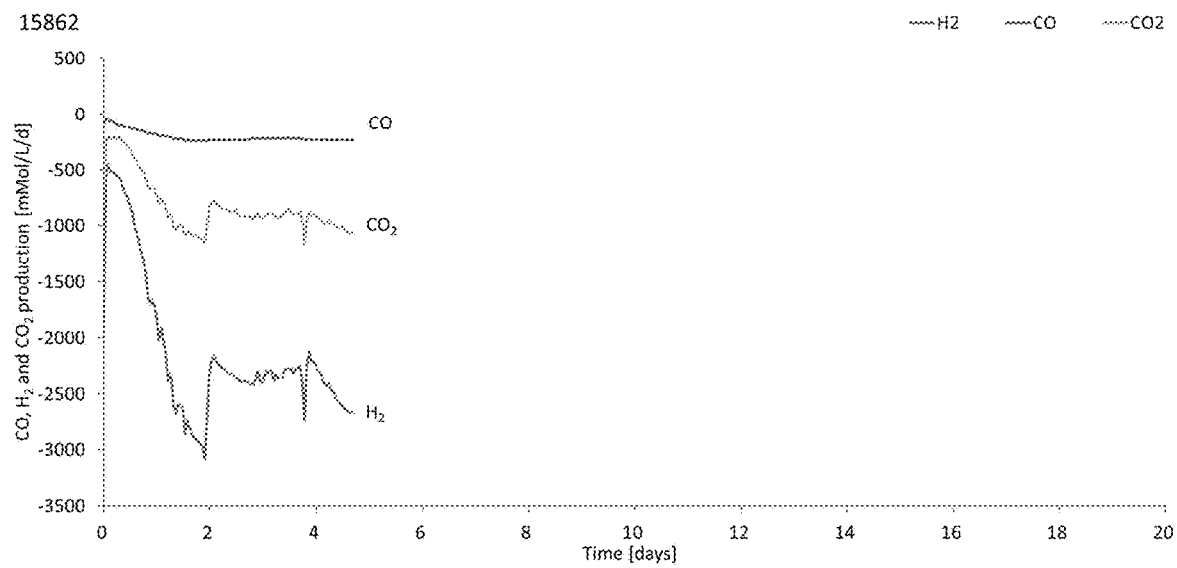

This example demonstrates the comparative performance of two reactors provided with a gaseous substrate comprising 68 vol. % $H_2$, 3.8 vol. % CO, 26 vol. % $CO_2$ and 1 vol. % $N_2$, an 18:1 molar ratio of $H_2$:CO. The only difference in the operating parameters of the two reactors was the conditions under which the inoculum for each reactor was produced. FIG. 6a and FIG. 6b show metabolite and gas profiles in a first bioreactor that received inoculum produced under CO-rich conditions. FIG. 7a and FIG. 7b show metabolite and gas profiles in a second bioreactor that received inoculum produced under $H_2$ rich conditions. Both reactors consume $H_2$, CO, and $CO_2$ with similar efficiency, but the reactor that received an inoculum from an $H_2$ rich inoculation reactor (FIG. 7a) has reduced selectivity to ethanol.

Example 2

Figure 8A:
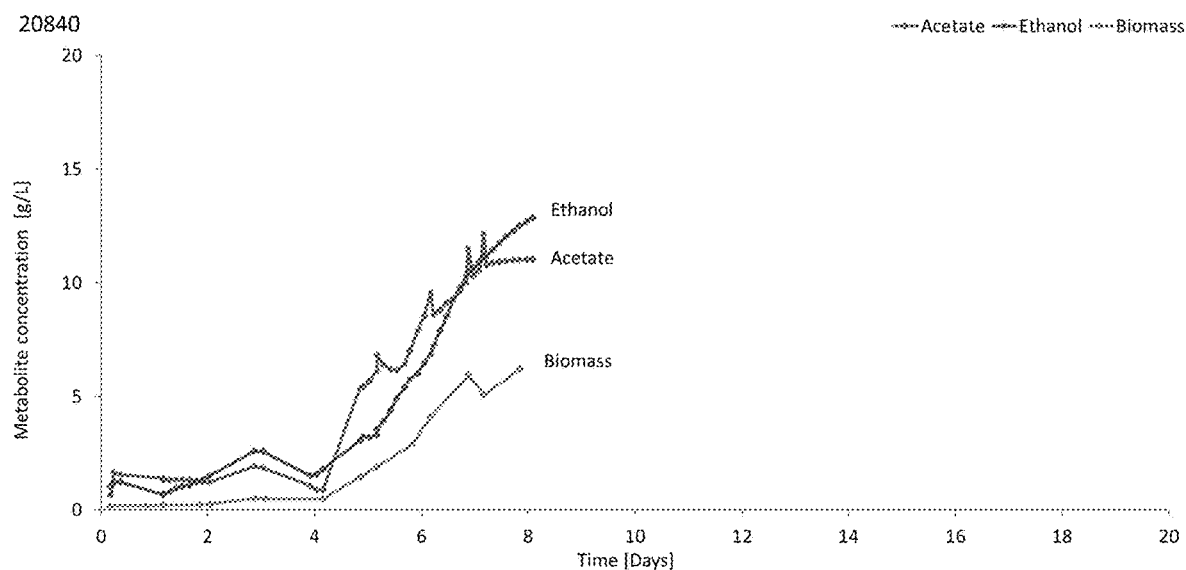
FIGS. 8a and 8b are graphs showing metabolite production and gas uptake in a first bioreactor according to Example 2.
Figure 8B:
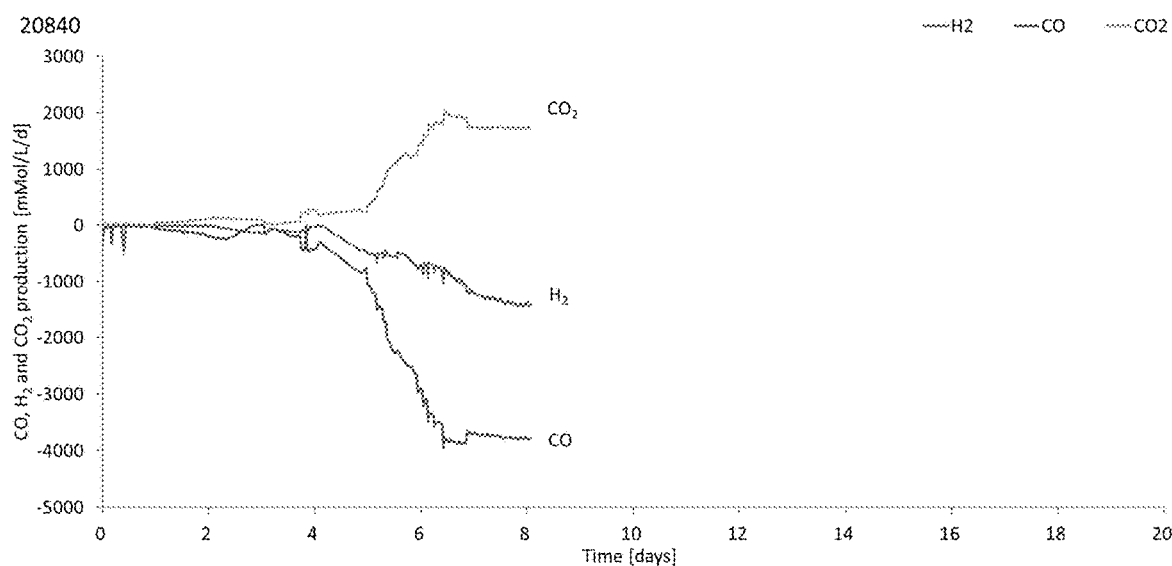
Figure 9A:
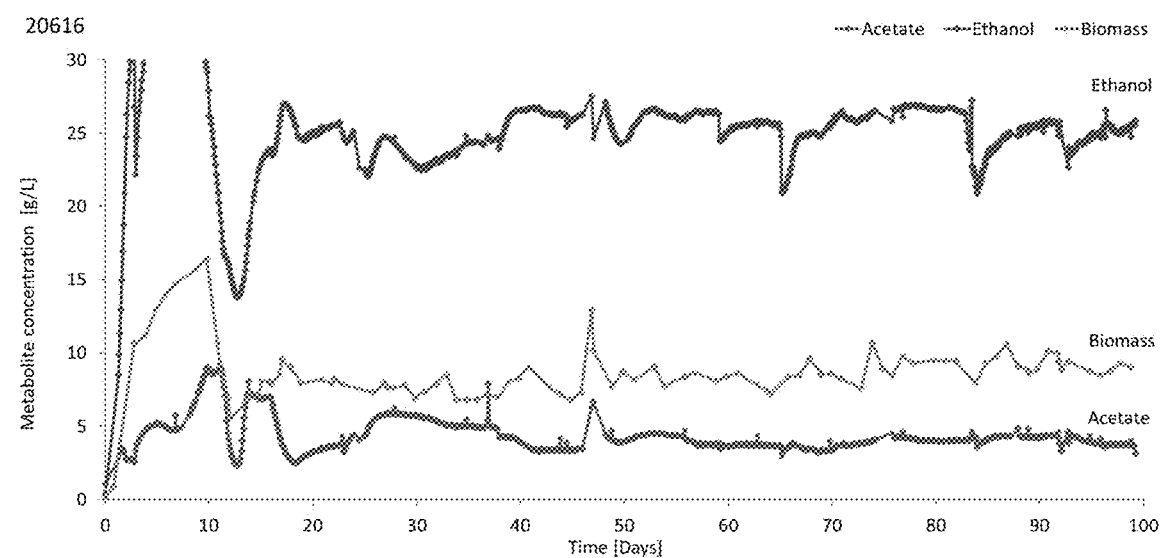
FIGS. 9a and 9b are graphs showing metabolite production and gas uptake in a second bioreactor according to Example 2.
Figure 9B:
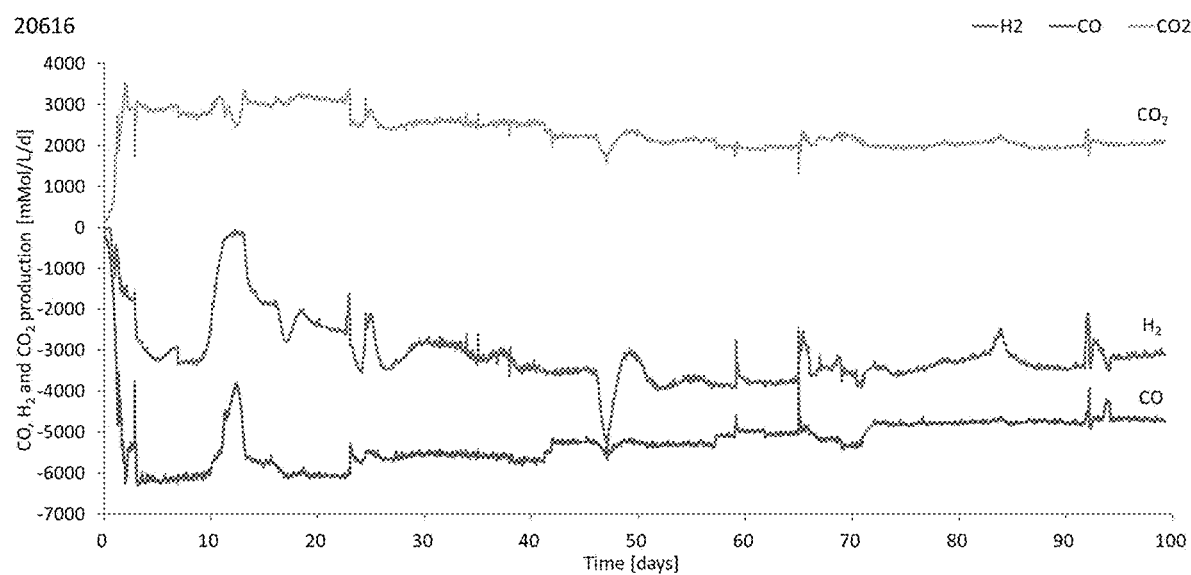

This example demonstrates the comparative performance of reactors provided with inoculum from inoculation reactors operated under differing gas conditions. FIG. 8a and FIG. 8b show the metabolite and gas profiles of a fermentation inoculated with a culture received from an inoculation produced with the following gas composition: 48 vol. % $H_2$, 40 vol. % CO, 2 vol. % $CO_2$, and 10 vol. % $N_2$. FIG. 9a and FIG. 9b illustrate the metabolite and gas profiles of a fermentation inoculated with a culture received from an inoculation produced under CO-rich conditions. The ethanol selectivity demonstrated by the reactor fed by CO-rich gas inoculation reactor (FIG. 9a) is much higher than that of the reactor that received an inoculum from an $H_2$ rich inoculation reactor (FIG. 8a).

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgment that that prior art forms part of the common general knowledge in the field of endeavor in any country.

The use of the terms "a" and "an" and "the" and similar referents in the context of describing the invention (especially in the context of the following claims) are to be construed to cover both the singular and the plural unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means ±20% of the indicated range, value, or structure, unless otherwise indicated.

The recitation of ranges of values herein is merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for producing one or more fermentation products, the process comprising;
   a. providing a CO-rich C1-containing gaseous substrate to an inoculation reactor comprising a liquid nutrient medium containing a culture of one or more C1-fixing microorganism;
   b. fermenting the CO-rich C1-containing gaseous substrate to produce an inoculum;
   c. passing at least a portion of the inoculum to a bioreactor system, the bioreactor system comprising at least one bioreactor containing a culture of one or more C1-fixing microorganism in a liquid nutrient medium;
   d. passing an $H_2$ rich C1-containing gaseous substrate to the bioreactor system; and
   e. fermenting the $H_2$ rich C1-containing gaseous substrate to produce at least one fermentation product.

2. The process of claim 1, wherein the CO-rich C1-containing gaseous substrate comprises $H_2$ at an $H_2$:CO molar ratio of less than 1:1.

3. The process of claim 1, wherein the CO-rich C1-containing gaseous substrate comprises $H_2$ at an $H_2$:CO molar ratio of less than 0.5:1.

4. The process of claim 1, wherein the CO-rich C1-containing gaseous substrate comprises $H_2$ at an $H_2$:CO molar ratio between 0.02:1 to 1:1.

5. The process of claim 1, wherein the $H_2$ rich C1-containing gaseous substrate comprises $H_2$ at an $H_2$:CO molar ratio of at least 1.1:1.

6. The process of claim 1, wherein the $H_2$ rich C1-containing gaseous substrate comprises $H_2$ at an $H_2$:CO molar ratio between 1.1:1 to 6:1.

7. The process of claim 1, wherein the C1-fixing microorganism is a carboxydotrophic bacterium.

8. The process of claim 7, wherein the carboxydotrophic bacterium is selected from the group consisting of *Moorella, Clostridium, Ruminococcus, Acetobacterium, Eubacterium, Butyribacterium, Oxobacter, Methanosarcina*, and *Desulfotomaculum*.

9. The process of claim 7, wherein the carboxydotrophic bacterium is *Clostridium autoethanogenum*.

10. The process of claim 1 wherein the bioreactor system comprises one or more primary bioreactors linked to one or more secondary bioreactors.

* * * * *